(12) United States Patent
Zhang et al.

(10) Patent No.: US 10,196,426 B1
(45) Date of Patent: Feb. 5, 2019

(54) CHIMERIC VECTOR AND PREPARATION METHOD AND USE THEREOF

(71) Applicant: SUN YAT-SEN UNIVERSITY, Guangdong (CN)

(72) Inventors: Hui Zhang, Guangdong (CN); Ting Pan, Guangdong (CN)

(73) Assignee: SUN YAT-SEN UNIVERSITY, Guangdong (CN)

( * ) Notice: Subject to any disclaimer, the term of this patent is extended or adjusted under 35 U.S.C. 154(b) by 102 days.

(21) Appl. No.: 15/503,005

(22) PCT Filed: Jun. 18, 2014

(86) PCT No.: PCT/CN2014/080199
§ 371 (c)(1),
(2) Date: Feb. 10, 2017

(87) PCT Pub. No.: WO2015/192339
PCT Pub. Date: Dec. 23, 2015

(51) Int. Cl.
| | | |
|---|---|---|
| *C12N 15/62* | (2006.01) | |
| *A61K 38/00* | (2006.01) | |
| *C07K 14/005* | (2006.01) | |
| *C12N 9/12* | (2006.01) | |

(52) U.S. Cl.
CPC .............. *C07K 14/005* (2013.01); *C12N 9/12* (2013.01); *C12Y 207/11001* (2013.01); *C07K 2319/00* (2013.01); *C12N 2740/16033* (2013.01)

(58) Field of Classification Search
CPC ..... C07K 2319/00; C12N 15/62; A61K 38/00
See application file for complete search history.

(56) References Cited

FOREIGN PATENT DOCUMENTS

| | | | |
|---|---|---|---|
| CN | 101001953 | 7/2007 | |
| CN | 101108882 | 1/2008 | |
| EP | 1652857 A2 * | 5/2006 | ............. A61K 39/21 |

OTHER PUBLICATIONS

"International Search Report (Form PCT/ISA/210)", dated Apr. 10, 2015, with English translation thereof, pp. 1-8.

* cited by examiner

*Primary Examiner* — Karen Cochrane Carlson
(74) *Attorney, Agent, or Firm* — JCIPRNET

(57) ABSTRACT

A chimeric vector is provided in the present invention, which is formed by ligating a Vif protein and a functional protein, the functional protein being a Raf protein or a Rev protein. By designing and constructing a Rev-Vif-C vector and then demonstrating that the Rev-Vif-C vector has a good anti-virus effect by a variety of experiments, the present invention proposes a novel anti-virus technology against the Rev protein of HIV-1. Moreover, by designing and constructing a RBD-Vif-C vector and then demonstrating that the RBD-Vif-C vector has a good tumor cell killing effect by cell-level experiments in vitro and experiments in vivo with nude mouse tumor models, the present invention proposes a novel anti-tumor technology specifically against mutant KRAS.

20 Claims, 8 Drawing Sheets
Specification includes a Sequence Listing.

FIG. 4

```
                         SEQUENCE LISTING

<160> NUMBER OF SEQ ID NOS: 9

<210> SEQ ID NO 1
<211> LENGTH: 537
<212> TYPE: DNA
<213> ORGANISM: Artificial Sequence
<220> FEATURE:
<223> OTHER INFORMATION: ROL1-Vif-C

<400> SEQUENCE: 1
atggcaggaa gaagcggaga cagcgacgaa gagctcatca gaacagtcag actcatcaag      60
cttctctatc aaagcaaccc acctcccaac cccgagggga cccgacaggc ccgaaggaat     120
agaagaagaa ggtggagaga gagacagaga cagatccatt cgattagtga acggatcctt     180
ggcacttatc tgggacattt gggtcaggga gtctccatag aatggaggaa aaagagatat     240
agcacacaag tagaccctga actagcagac caactaattc atctgtatta ctttgactgt     300
ttttcagact ctgctataag aaaggcctta ttaggacaca tagttagccc taggtgtgaa     360
tatcaagcag gacataacaa ggtaggatct ctacaatact tggcactagc agcattaata     420
acaccaaaaa agataaagcc acctttgcct agtgttacga aactgacaga ggatagatgg     480
aacaagcccc agaagaccaa gggccacaga gggagccaca caatgaatgg acactag        537

<210> SEQ ID NO 2
<211> LENGTH: 405
<212> TYPE: DNA
<213> ORGANISM: Artificial Sequence
<220> FEATURE:
<223> OTHER INFORMATION: ROL2-Vif-C

<400> SEQUENCE: 2
atggacagcg acgaagagct catcagaaca gtcagactca tcaagcttct ctatcaaagc      60
aaccatttgg gtcagggagt ctccatagaa tggaggaaaa agagatatag cacacaagta     120
gaccctgaac tagcagacca actaattcat ctgtattact ttgactgttt ttcagactct     180
gctataagaa aggccttatt aggacacata gttagcccta ggtgtgaata tcaagcagga     240
cataacaagg taggatctct acaatacttg gcactagcag cattaataac accaaaaaag     300
ataaagccac ctttgcctag tgttacgaaa ctgacagagg atagatggaa caagccccag     360
aagaccaagg gccacagagg gagccacaca atgaatggac actag                     405

<210> SEQ ID NO 3
<211> LENGTH: 387
<212> TYPE: DNA
<213> ORGANISM: Artificial Sequence
<220> FEATURE:
<223> OTHER INFORMATION: ROL12-Vif-C

<400> SEQUENCE: 3
atgatccatt cgattagtga acggatcctt ggcacttatc tgggacattt gggtcaggga      60
gtctccatag aatggaggaa aaagagatat agcacacaag tagaccctga actagcagac     120
caactaattc atctgtatta ctttgactgt ttttcagact ctgctataag aaaggcctta     180
ttaggacaca tagttagccc taggtgtgaa tatcaagcag gacataacaa ggtaggatct     240
```

-continued

```
ctacaatact tggcactagc agcattaata acaccaaaaa agataaagcc acctttgcct    300
agtgttacga aactgacaga ggatagatgg aacaagcccc agaagaccaa gggccacaga    360
gggagccaca caatgaatgg acactag                                        387
```

<210> SEQ ID NO 4
<211> LENGTH: 914
<212> TYPE: DNA
<213> ORGANISM: Artificial Sequence
<220> FEATURE:
<223> OTHER INFORMATION: Fusion expression vector PTD-RBD-Vif-C

<400> SEQUENCE: 4

```
atgggccgta aaaaacgtcg tcagcgtcgt cgtggccata gcggccgtaa aaaacgtcgt     60
cagcgtcgtc gtggccatat ttatccgtat gatgtgccgg attatgcggg cgatccgggc    120
cgtaaaaaac gtcgtcagcg tcgtcgtaag cttatggagc acatacaggg agcttggaag    180
acgatcagca atggttttgg attcaaagat gccgtgtttg atggctccag ctgcatctct    240
cctacaatag ttcagcagtt tggctatcag cgccgggcat cagatgatgg caaactcaca    300
gatccttcta agacaagcaa cactatccgt gttttcttgc cgaacaagca aagaacagtg    360
gtcaatgtgc gaaatggaat gagcttgcat gactgcctta tgaaagcact caaggtgagg    420
ggcctgcaac cagagtgctg tgcagtgttc agacttctcc acgaacacaa aggtaaaaaa    480
gcacgcttag attggaatac tgatgctgcg tctttgattg gagaagaact tcaagtagat    540
ttcctgcgaa ttctgcagtc gacggtaccg cggcatttgg gtcagggagt ctccatagaa    600
ggaggaaaaa gagatatagc acacaagtag accctgaact agcagaccaa ctaattcatc    660
tgtattactt tgactgtttt tcagactctg ctataagaaa ggccttatta ggacacatag    720
ttagccctag gtgtgaatat caagcaggac ataacaaggt aggatctcta caatacttgg    780
cactagcagc attaataaca ccaaaaaaga taaagccacc tttgcctagt gttacgaaac    840
tgacagagga tagatggaac aagccccaga agaccaaggg ccacagaggg agccacacaa    900
tgaatggaca ctag                                                      914
```

<210> SEQ ID NO 5
<211> LENGTH: 79
<212> TYPE: PRT
<213> ORGANISM: Artificial Sequence
<220> FEATURE:
<223> OTHER INFORMATION: N-terminus of Vif protein of HIV-1

<400> SEQUENCE: 5

```
Met Glu Asn Arg Trp Gln Val Met Ile Val Trp Gln Val Asp Arg Met
1               5                   10                  15

Arg Ile Arg Thr Trp Lys Ser Leu Val Lys His His Met Tyr Val Ser
            20                  25                  30

Gly Lys Ala Arg Gly Trp Phe Tyr Arg His His Tyr Glu Ser Pro His
        35                  40                  45

Pro Arg Ile Ser Ser Glu Val His Ile Pro Leu Gly Asp Ala Arg Leu
    50                  55                  60

Val Ile Thr Thr Tyr Trp Gly Leu His Thr Gly Glu Arg Asp Trp
65                  70                  75
```

<210> SEQ ID NO 6
<211> LENGTH: 18
<212> TYPE: PRT
<213> ORGANISM: Artificial Sequence
<220> FEATURE:

<223> OTHER INFORMATION: N-terminal oligomerization domain of Rev
      protein of HIV-1

<400> SEQUENCE: 6

Asp Glu Glu Leu Ile Arg Thr Val Arg Leu Ile Lys Leu Leu Tyr Gln
1               5                   10                  15

Ser Asn

<210> SEQ ID NO 7
<211> LENGTH: 15
<212> TYPE: PRT
<213> ORGANISM: Artificial Sequence
<220> FEATURE:
<223> OTHER INFORMATION: C-terminal oligomerization domain of Rev
      protein of HIV-1

<400> SEQUENCE: 7

Gln Ile His Ser Ile Ser Glu Arg Ile Leu Gly Thr Tyr Leu Gly
1               5                   10                  15

<210> SEQ ID NO 8
<211> LENGTH: 57
<212> TYPE: PRT
<213> ORGANISM: Artificial Sequence
<220> FEATURE:
<223> OTHER INFORMATION: N-terminal and C-terminal oligomerization
      domains of Rev protein
      of HIV-1

<400> SEQUENCE: 8

Asp Glu Glu Leu Ile Arg Thr Val Arg Leu Ile Lys Leu Leu Tyr Gln
1               5                   10                  15

Ser Asn Pro Pro Pro Asn Pro Glu Gly Thr Arg Gln Ala Arg Arg Asn
            20                  25                  30

Arg Arg Arg Arg Trp Arg Glu Arg Gln Arg Gln Ile His Ser Ile Ser
        35                  40                  45

Glu Arg Ile Leu Gly Thr Tyr Leu Gly
    50                  55

<210> SEQ ID NO 9
<211> LENGTH: 113
<212> TYPE: PRT
<213> ORGANISM: Artificial Sequence
<220> FEATURE:
<223> OTHER INFORMATION: C-terminus of Vif protein of HIV-1

<400> SEQUENCE: 9

His Leu Gly Gln Gly Val Ser Ile Glu Trp Arg Lys Lys Arg Tyr Ser
1               5                   10                  15

Thr Gln Val Asp Pro Glu Leu Ala Asp Gln Leu Ile His Leu Tyr Tyr
            20                  25                  30

Phe Asp Cys Phe Ser Asp Ser Ala Ile Arg Lys Ala Leu Leu Gly His
        35                  40                  45

Ile Val Ser Pro Arg Cys Glu Tyr Gln Ala Gly His Asn Lys Val Gly
    50                  55                  60

Ser Leu Gln Tyr Leu Ala Leu Ala Ala Leu Ile Thr Pro Lys Lys Ile
65                  70                  75                  80

Lys Pro Pro Leu Pro Ser Val Thr Lys Leu Thr Glu Asp Arg Trp Asn
                85                  90                  95

```
Lys Pro Gln Lys Thr Lys Gly His Arg Gly Ser His Thr Met Asn Gly
            100                 105                 110
His
```

CHIMERIC VECTOR AND PREPARATION METHOD AND USE THEREOF

CROSS-REFERENCE TO RELATED APPLICATION

This application is a 371 application of the International PCT application serial no. PCT/CN2014/080199, filed on Jun. 18, 2014. The entirety of the above-mentioned patent application is hereby incorporated by reference herein and made a part of this specification.

TECHNICAL FIELD

The present invention relates to a protein anti-cancer medicine, and more specifically, relates to a chimeric vector, and preparation method and use thereof.

BACKGROUND

All this time, if change happens in cell genome which controls the expression or the function in cell growth and cell differentiation, it is considered as the major cause inducing tumor. Molecular biology study in tumor is directed to confirm those changes of genes in various tumor types and to illustrate the functions of these genes in tumorigenesis. In particular, RAS gene is one of the most common gene families in tumor mutation of human.

Under normal physiology circumstances, when a signaling pathway such as EGFR is activated after cells are stimulated by the external, the wild-type KRAS is phosphorylated by a tyrosine kinase such as active EGFR, before being transiently activated. The activated KRAS can activate the downstream signaling protein in the signaling pathway, after that the KRAS is inactivated rapidly. The activation/inactivation effect of the KRAS is controllable. However, mutant KRAS protein causes a dysfunction of protein that the mutant KRAS is still under activated status without the stimulation of activation signal from EGFR, such that the functional status of mutant KRAS is uncontrollable which makes the tumors proliferate continuously. The RAS gene, like a "switch" in vivo, plays an important regulating role in the signal transduction path of processes such as tumor cell growth and angiogenesis. The encoded protein of normal KRAS gene can inhibit tumor cell growth. Once the KRAS gene mutates, it will continuously stimulate the cell growth, disorganize the growth rhythm and thus cause tumorigenesis. Because the mutation of the KRAS gene generally occurs at the early stage of the tumor malignancy, also the KRAS genes of the primary tumor and the metastases are highly consistent; and it is generally acknowledged that the status of KRAS gene will not change with the treatment. Therefore, the detection of the mutation in the KRAS gene is an important indicator for in-depth understanding of the condition of oncogene as well as the development, prognosis and the curative effect of the chemoradiotherapy for various cancers, having a vitally important clinical significance.

In China, pancreatic cancer has always been one of the top ten malignant tumors that causing the population death, having a five-year survival rate of less than 5%, being one of the worst malignant tumors in prognosis. In recent years, colorectal cancer has become the second biggest cancer killer in Guangdong area with obviously increasing trend, having a morbidity and a mortality that significantly increase year by year. The RAS gene of tumor cells has a mutation rate of about 25% while pancreatic cancer, colorectal cancer and non-small alveolar lung cancer have a mutation rate of 90%, 45% and 35%, respectively.

In late 1970s and early 1980s, a disease with a dysfunction of the immune system as a major characteristic arose in Europe and the United States. Afterwards, scientists from various countries started to explore the nosogenesis and the therapeutic schedule for such disease. Until 1983, after the Pasteur Research Group in France first successfully isolated this new retrovirus, the theoretical study and the medical treatment for HIV-1 became more and more. Nowadays, medicine against HIV-1 mainly acts on different stages of the life cycle of the virus, and specifically on some necessary enzymes such as reverse transcriptase and protease.

Although there are many anti-HIV-1 medicines that are commercial available nowadays and HARRT is widely used, the resulting problems such as drug resistance, huge medical expenses and the side effects of the medicines should not be underestimated. Plasma viral load in a considerable number of patients can be reduced below a detectable level by highly active antiretroviral therapy (HARRT), but the rebound after stopping taking such medicine and the severe toxic side effects are still can't be solved. Gene therapy has shown its potential for anti-virus and some research achievement has entered clinical test stage, but its low efficiency and the adverse reaction possibly brought by the foreign vector are still the major obstacle to research and development. Nowadays, there are four major hot spots for the research and development of anti-HIV-1 medicine internationally: 1) inhibitor that inhibits virus entering into the cells; 2) neutralizing antibody; 3) integrase inhibitor; and 4) chemical chemokine receptor antagonists. Scientists still keep trying to explore an anti-virus medicine that is safer, more effective and more affordable.

Regulator of expression of virion proteins (Rev) is an indispensable regulatory protein in the transcription process of HIV-1. The Rev interacts with RRE of mRNA of the virus so as to aid unspliced or partially spliced mRNA of HIV-1 to transfer out of the nucleus. If the expression of the Rev is inhibited, the unspliced or partially spliced mRNA of HIV-1 will be unable to transfer out of the nucleus, leading to a complete degradation within the nucleus, and a further block of the replication of HIV-1. Therefore, how to inhibit the expression of Rev protein will be an important target for research and development of anti-HIV-1 medicine.

SUMMARY OF THE INVENTION

One of the objectives in the present invention is to invent a medicine that uses Vif in HIV-1.

First a chimeric vector is provided, which comprises nucleic acid encoding a Vif protein and a functional protein. The functional protein is a Raf protein or a Rev protein.

An end of the functional protein is ligated to the Vif protein.

The chimeric vector is obtained by replacing nucleic acid encoding an N-terminus of the Vif protein with nucleic acid encoding a binding domain of an N-terminus of the Raf protein which can specifically bind to GTP-Kras. Such chimeric vector is named as Rev-Vif-C.

The chimeric vector is obtained by replacing nucleic acid encoding the N-terminus of the Vif with nucleic acid encoding a multimerization domain of the Rev. Such chimeric vector is named as RBD-Vif-C.

Further a method for the production of a fusion protein comprising Vif and Revof, the method comprising steps as follows:

a) preparing a chimeric vector, comprising respectively replacing nucleic acid encoding an amino acid sequence at positions 1-79 (SEQ ID NO: 5) of an N-terminus of a Vif protein with nucleic acid encoding two oligomerization domains which are provided on a protein structure of a Rev, thus three new chimeric vectors ROL1-Vif-C, ROL2-Vif-C and ROL12-Vif-C are constructed, the ROL1-Vif-C comprising nucleic acid encoding an oligomerization domain of a Rev N-terminus, the ROL2-Vif-C comprising nucleic acid encoding an oligomerization domain of a Rev C-terminus, the ROL12-Vif-C comprising nucleic acid encoding two oligomerization domains of the Rev N-terminus and the Rev C-terminus, the oligomerization domain of the Rev N-terminus is amino acids at positions 9-26 (SEQ ID NO: 6) of an amino acid sequence of the Rev protein, the oligomerization domain of the Rev C-terminus is amino acids at positions 51-65 (SEQ ID NO: 7) of the amino acid sequence of the Rev protein, the two oligomerization domains of the Rev N-terminus and the Rev C-teiminus are amino acids at positions 9-65 (SEQ ID NO: 8) of the amino acid sequence of the Rev protein, and a Vif-C moiety is amino acids at positions 80-193 (SEQ ID NO: 9) of the amino acid sequence of the Vif protein;

b) cloning these three chimeric vectors into an expression vector pcDNA3.1 respectively wherein, sequences of the three vectors are shown as SEQ ID NO:1, SEQ ID NO:2 and SEQ ID NO:3, and enzyme cutting sites used for ligating the vectors to the pcDNA3.1 are bamH I and Xhol I;

c) performing a transient expression by transfecting a host cell with the three vectors mentioned above;

d) culturing the host cell under conditions that the fusion protein is produced; and e) isolating the fusion protein from the host cell culture.

Also a method for the production of a fusion protein comprising Vif and Raf, the method comprising steps as follows:

a) preparing a chimeric vector, comprising respectively replacing nucleic acid encoding replacing an amino acid sequence at positions 1-79 of an N-terminus of a Vif protein with nucleic acid encoding a RAS binding domain RBD which is provided on a protein structure of a Raf and specifically binds to GTP-KRAS, thus a new chimeric vector of RBD-Vif-C is constructed;

b) cloning the chimeric vector into an expression vector pcDNA3.1 and performing a transient expression by transfecting a host cell with the vector mentioned above;

c) ligating nucleic acid encoding a transmembrane peptide segment PTD to an *Escherichia coli* expression vector of pet-32a;

d) performing PCR amplification using the RBD-Vif-C as a template, ligating the RBD-Vif-C of the obtained PCR product to the expression vector pet-32a, and the PTD being located on an N-terminus of the RBD-Vif-C to form a fusion expression vector PTD-RBD-Vif-C;

e) transforming plasmids of the PTD-RBD-Vif-C into the *Escherichia coli* BL21(DE3);

f) culturing the transformed *Escherichia* con; and g) using a nickel column to pufify a single PTD-RBD-Vif-C protein from the *Escherichia coli* culture.

In particular, culturing mentioned in f) is to inoculate a single colony of the transformed *Escherichia coli* to a LB liquid medium containing ampicillin for culturing overnight; and then the colony is inoculated to a 37° C. preheated LB liquid medium containing ampicillin with a volume ratio of 1:50 for culturing until OD600 reaches 0.6; IPTG is added to the expressed PTD-RBD-Vif-C protein until having a final concentration of 0.4 mmol/L, and the bacteria is collected after induction.

A method of purification mentioned in g) is to wash total bacteria with PBS Buffer. After being resuspended and ultrasonic treated, a lysate supernatant is obtained by a high speed centrifugation, and an eluted protein is collected after an affinity chromatography purification using the nickel column.

Sequence of the fusion expression vector PTD-RBD-Vif-C is shown as SEQ ID NO:4.

Structures from the N-terminus to the C-terminus are transmembrane peptide PTD moiety, KRAS binding moiety of the RBD and degradation moiety of the Vif-C, respectively.

Vif protein is an important protein of HIV-1 itself, can bind to target proteins and ligate them to an E3 ligase complex (Vif-SCF-CUL5 complex). Then such complex will make the target proteins ubiquitinated, thus leading to the degradation of the proteins in a proteasome. The present invention mainly focuses on the corresponding cancers caused by the mutation of KRAS, attempts to replace the N-terminus of the Vif with the RBD of the N-terminus of the Raf protein which can specifically bind to the GTP-Kras, and by means of several tests in vitro and in vivo, explores the efficiency and the acting mechanisms for protein obtain from such chimeric type vector degrading the mutant KRAS. This technical invention has a very important significance for further researching and developing an anti-tumor protein medicine. Thus, this new method of constructing the chimeric vector that is provided in the present invention will very likely be a new technology of anti-tumor with extremely significant academic value and practical value.

(1) In order to overcome the defect and deficiency in the prior art, the objective of the present invention is to provide a method of constructing a new type of chimeric vector and use thereof in the life science research and the clinical treatment for tumor.

(2) A new tumor-killing technology corresponding to KRAS gene is provided in the present invention.

(3) A new technology of degrading the expression of KRAS protein is provided in the present invention.

(4) A new technology that can specifically degrade the protein in particular condition or in particular modification on the protein level is provided in the present invention.

(5) A new method of degrading multiple proteins is provided in the present invention, i.e. inserting a binding site of a certain protein to the N-terminus of the Vif so as to realize the degradation process of specific protein by the ubiquitination path of the C-terminus of the Vif.

(6) Use of a new technology for treating pancreatic cancer tumor is provided in the present invention.

(7) Use of a new technology for treating large intestine cancer (colorectal cancer) tumor is provided in the present invention.

(8) Use of a new technology for treating lung cancer tumor is provided in the present invention.

As for another technical solution:

Vif protein is an important protein of HIV-1 itself, can bind to the target proteins and ligate them to an E3 ligase complex (Vif-SCF-CUL5 complex). Then such complex will make the target proteins ubiquitinated, thus leading to the degradation of the proteins in proteasome. Mainly according to the ubiquitination function of the Vif protein, the present invention replaces the N-terminus of the Vif with the multimerization domain of the Rev such that it can specifically bind to the Rev protein of HIV-1 and then degrade the Rev by the ubiquitination function of the Vif. Attack its shield with its own spears. Thus the objective of inhibiting HIV-1 replication can be achieved with strong novelty and specificity. Also it provides a new idea and method of researching and developing the anti-HIV-1 medicine.

(1) In order to overcome the defect and deficiency in the prior art, the objective of the present invention is to provide a method of constructing a new type of chimeric vector and use thereof in the life science research and the clinical treatment.

(2) A new method of protecting cells from the attack of HIV-1 is provided in the present invention. After the CD4+T cells in the patient are sorted out for amplification in vitro, they are allowed to express the Rev-Vif-C vector stably and then transfused back into the patient. This can not only protect the patient from the second attack of HIV-1, but also help the patient clear the HIV-1 virus in the body.

(3) A new vector against the spontaneous mutation of HIV-1 is provided in the present invention. The drug resistance of HIV-1 is mostly due to its spontaneous mutation caused by the drugs. But the provided chimeric vector is constructed by using the mutual combination of the domains of the Rev itself. It can avoid various possible mutations, and thus can present an excellent inhibitory effect on multiple mutant strains of HIV-1.

(4) A new technology of degrading the expression of the Rev protein is provided in the present invention.

(5) A new technology of degrading multiple proteins is provided in the present invention, i.e. inserting a binding site of a certain protein to the N-terminus of the Vif so as to realize the degradation process of specific protein by the ubiquitination pathway of the C-terminus of the Vif.

BRIEF DESCRIPTION OF THE DRAWINGS

Figure 4:
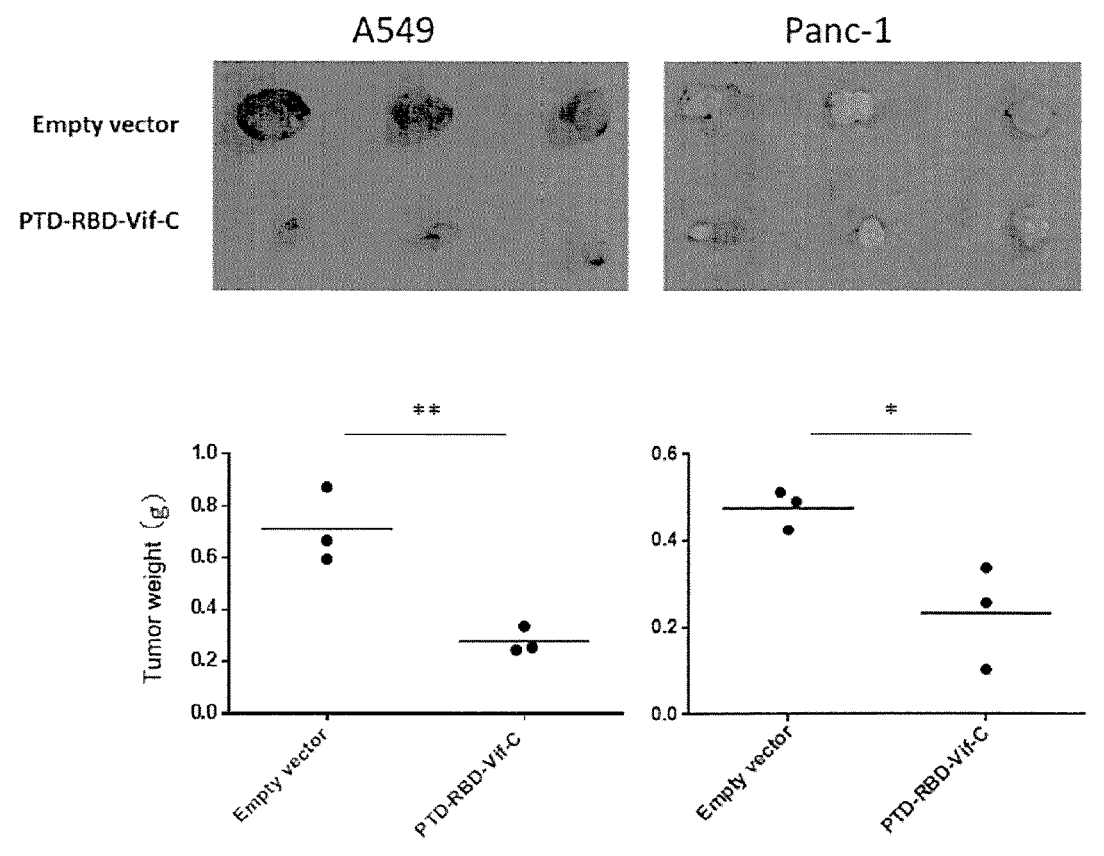

FIG. 4 illustrates that the protein PTD-RBD-Vif-C has a good anti-tumor effect in mice.

DETAILED DESCRIPTION OF THE PREFERED EMBODIMENT

Figure 1:
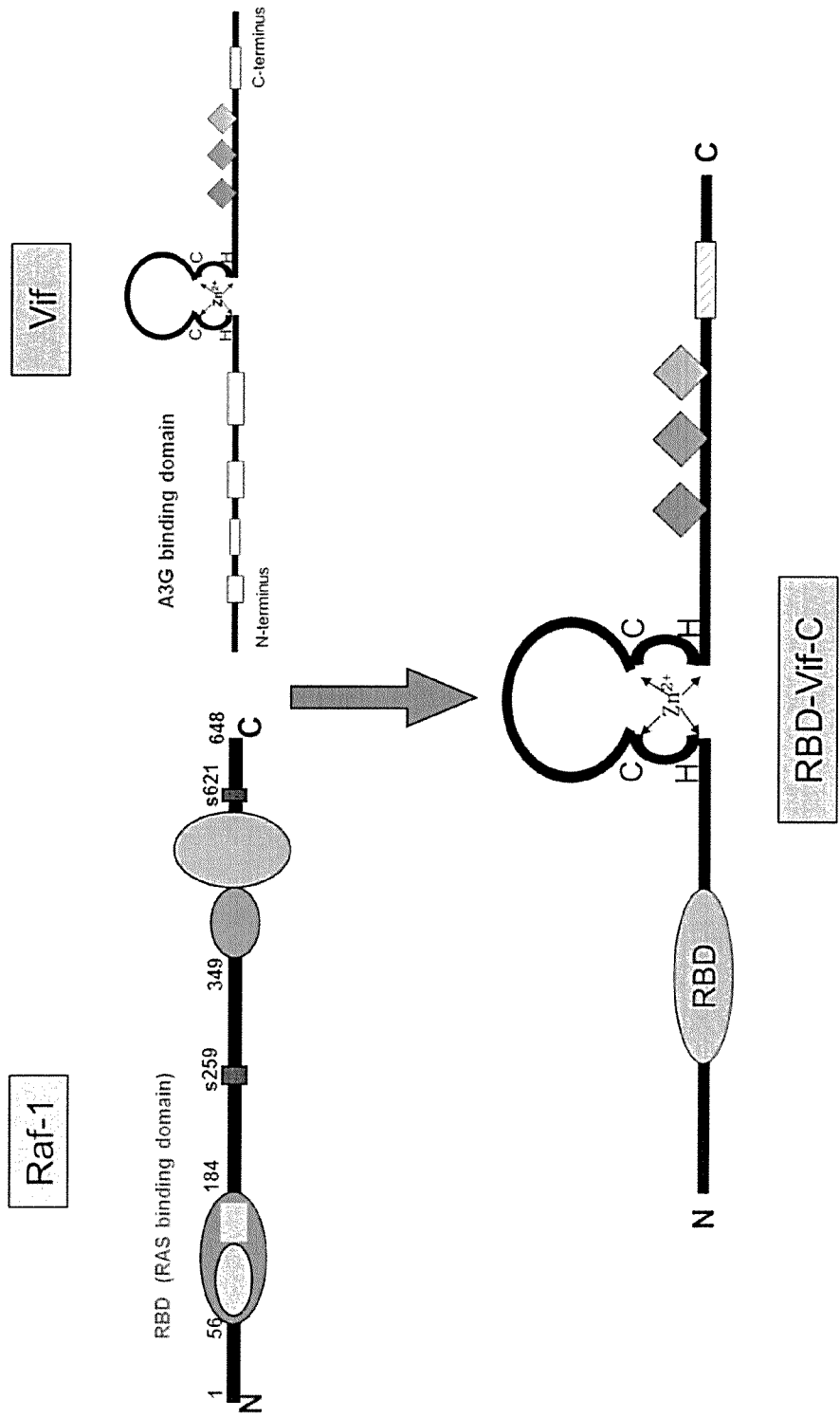
FIG. 1 illustrates the construction model of the chimeric vector RBD-Vif-C.
Figure 2:
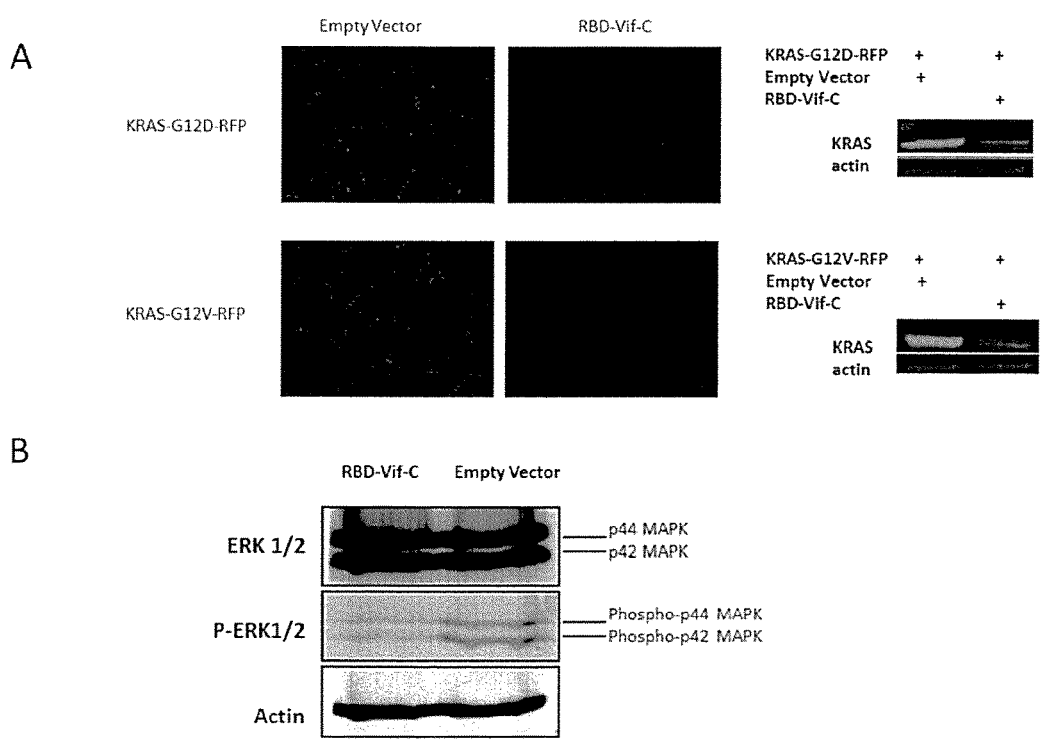
FIG. 2 illustrates that the protein encoded by the chimeric vector RBD-Vif-C can degrade the KRAS protein and inhibit its signaling pathway of phosphorylation in the downstream.
Figure 3:
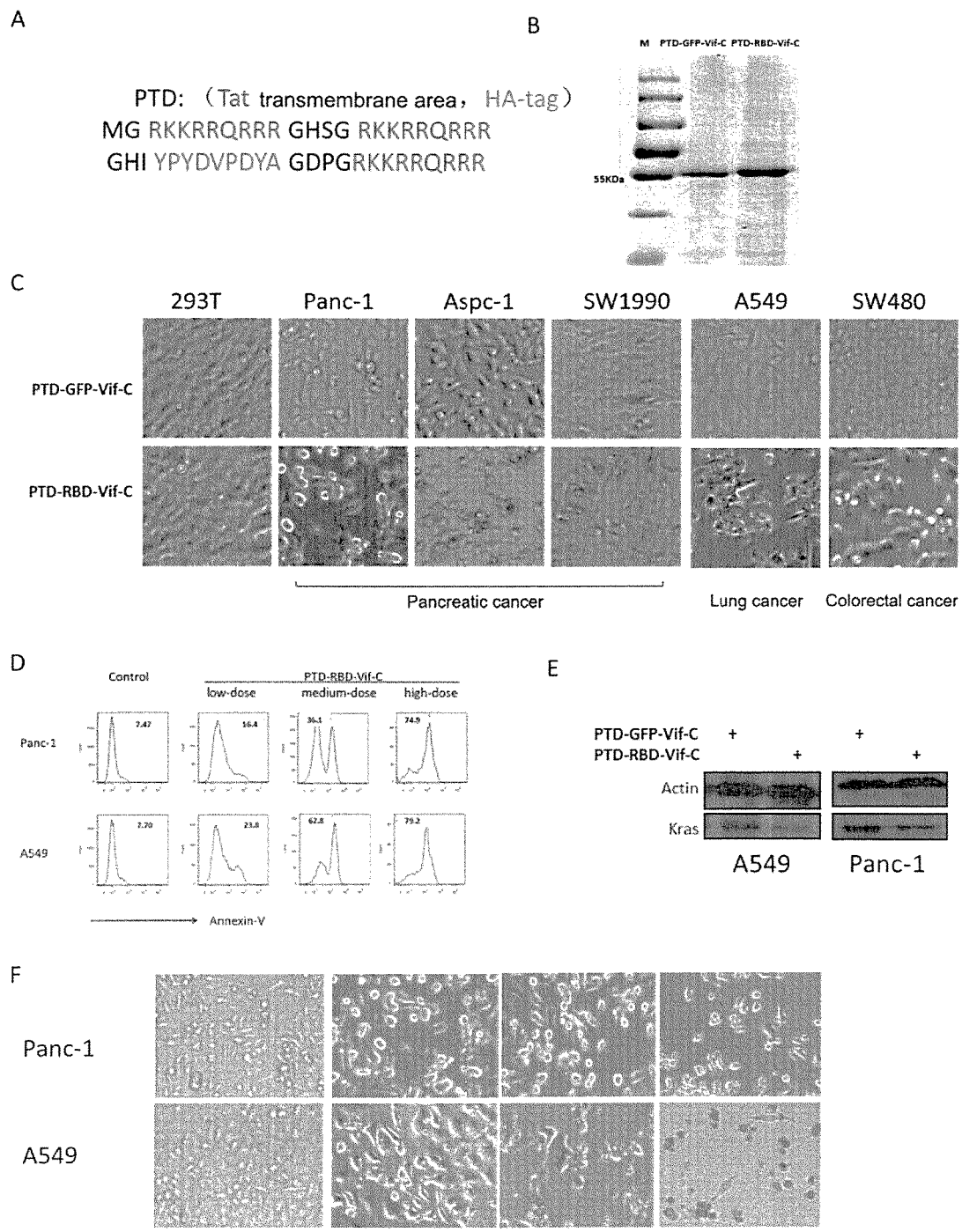
FIG. 3 illustrates that the protein PTD-RBD-Vif-C has a good killing effect on the tumor cells in vitro.
Figure 5:
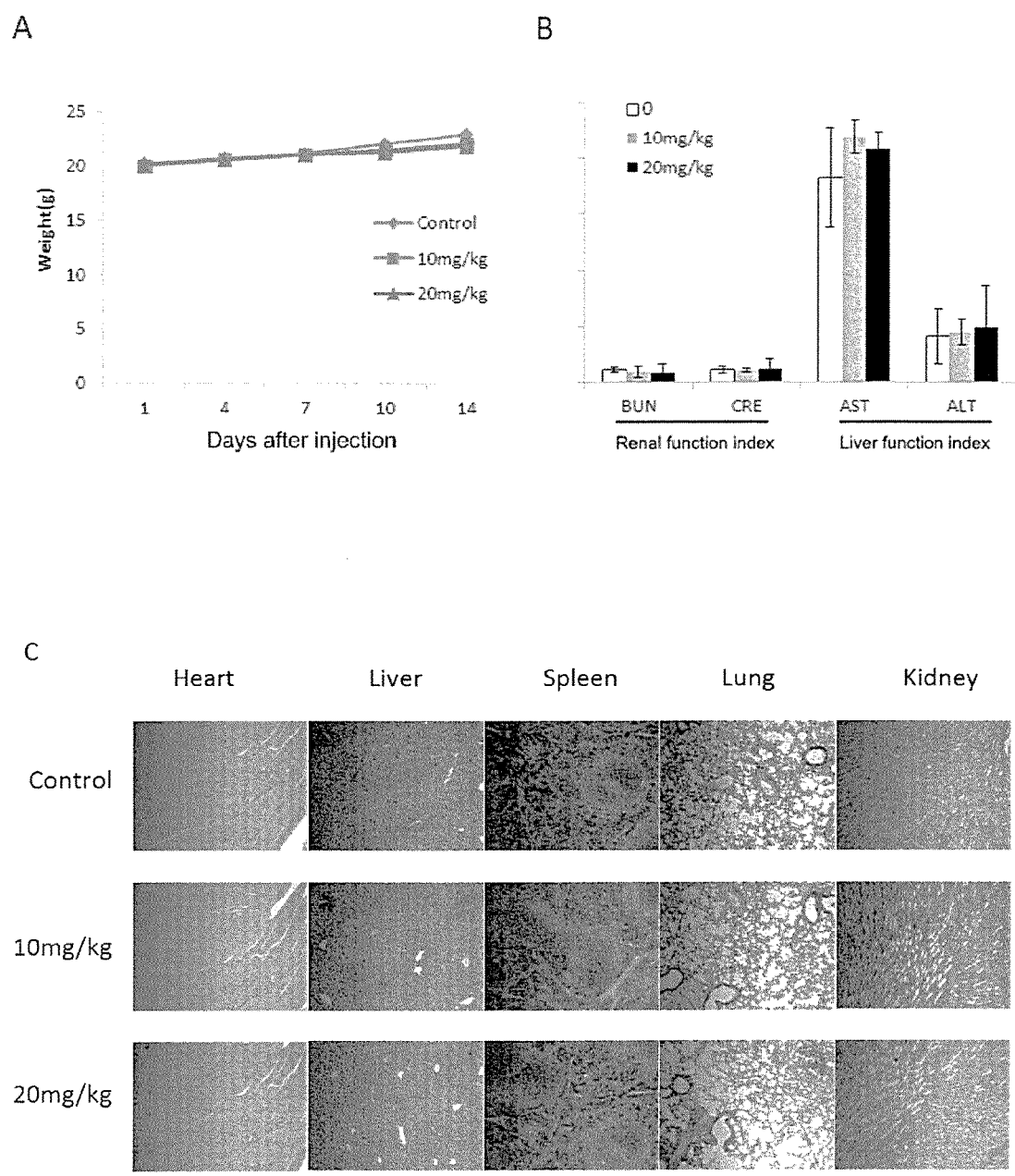
FIG. 5 illustrates that the acute toxicity test of the protein PTD-RBD-Vif-C in mice.
Figure 6:
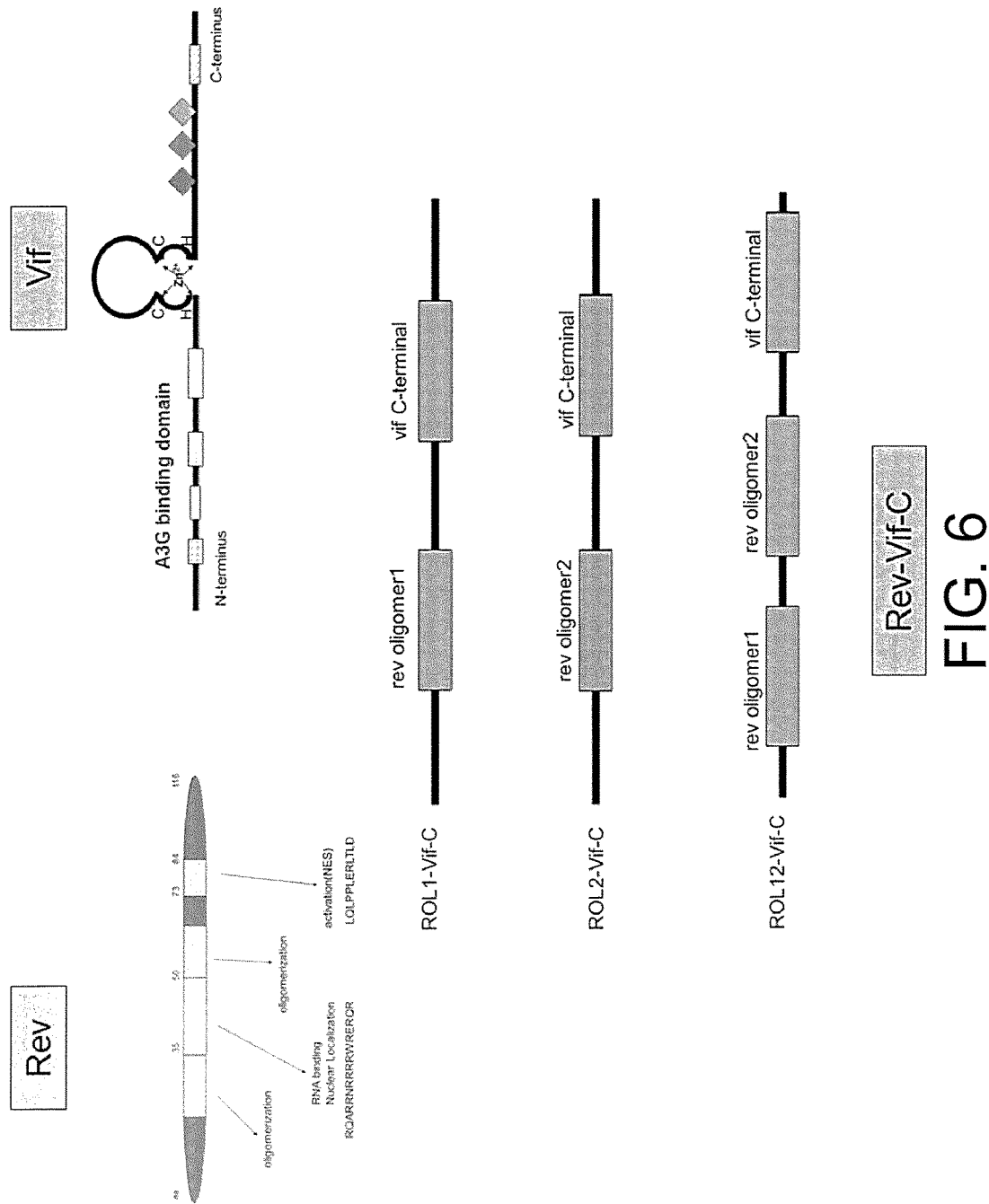
FIG. 6 illustrates the construction model of the chimeric vector Rev-Vif-C.
Figure 7:
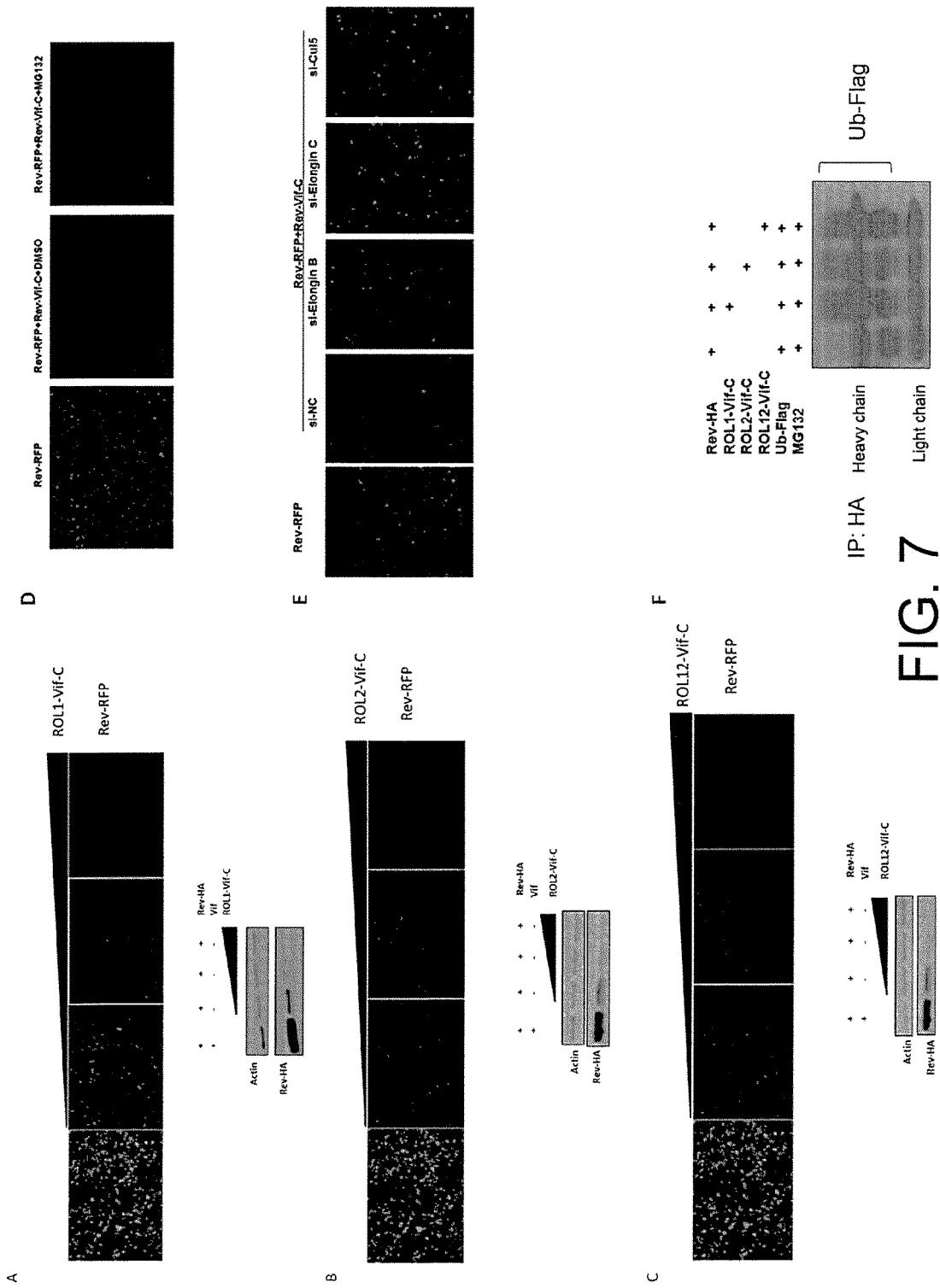
FIG. 7 illustrates that the protein encoded by the chimeric vector Rev-Vif-C degrades the protein Rev by the ubiquitination pathway.
Figure 8:
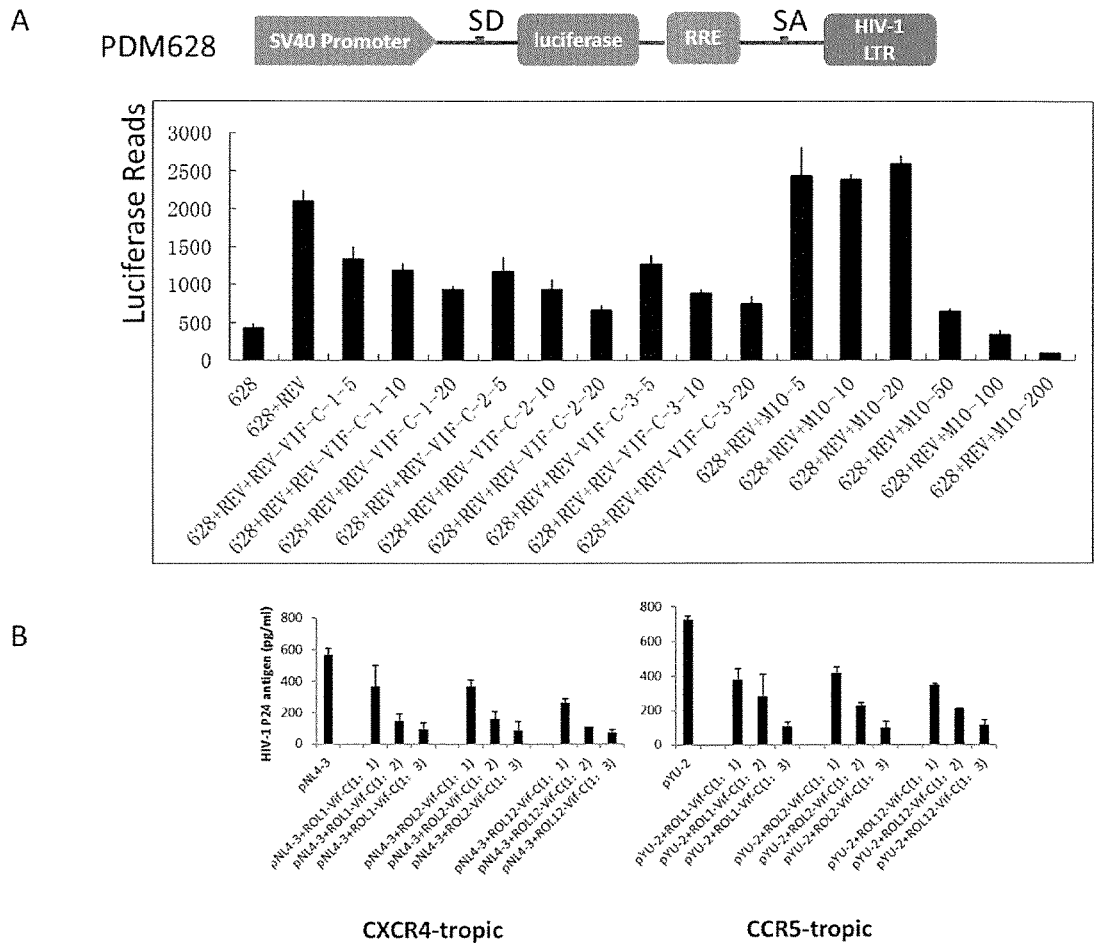
FIG. 8 illustrates that the protein encoded by the chimeric vector Rev-Vif-C inhibits the replication of multiple viral strains of wild-type HIV-1 by inhibiting the nuclear export function of the Rev-RRE.

The present invention will be further described in detail in combination with the accompanying drawings and specific embodiments below. Unless otherwise specified, reagents, equipment and methods used in the present invention are conventionally commercial reagents, equipment and routinely used methods in the present technical field.

Embodiment 1 A Construction Model of the Chimeric Vector RBD-Vif-C

As is well-known, the occurring of various tumors such as pancreatic cancer, lung cancer and colorectal cancer is greatly related to mutation of the KRAS gene. A single point mutation of KRAS is sufficient to lead to occurrence of a tumor, wherein the mutation of an amino acid at position 12 of the KRAS accounts for 98% of the single point mutation of KRAS. Among the mutation types of the amino acid at position 12, G12V and G12D mutations are the most significant, which accounts for 30% and 51% respectively. Specific degradation of mutant KRAS protein is realized by a degradation mechanism of target protein induced by Vif, and thus a new type of anti-tumor medicine is developed.

In accordance with the literatures, it is known that there is a KRAS binding domain RBD specifically binding to the mutant KRAS on an N-terminus of a RAF-1 protein. Such binding domain can specifically bind to the mutant KRAS protein in vivo and vitro, and its binding affinity for GTP-Kras is 100 times different from that for GDP-Kras. Hence, nucleic acid encoding the N-terminus of the Vif protein is replaced with nucleic acid encoding the RBD, and then it is ligated to the vector of pcDNA3.1 to form a chimeric vector RBD-Vif-C.

Specific steps are provided below:

(1) preparing a chimeric vector, in which nucleic acid encoding an amino acid sequence at positions 1-79 of the N-terminus of the Vif protein is replaced with nucleic acid encoding the RAS binding domain RBD which is provided on a protein structure of Raf and specifically binds to GTP-KRAS, thus a new chimeric vector RBD-Vif-C is constructed;

(2) cloning the chimeric vector into the expression vector pcDNA3.1 and performing a transient expression by transfection;

(3) synthesizing nucleic acid encoding a transmembrane peptide segment PTD and then ligating it to an *Escherichia coli* expression vector of pet-32a;

(4) performing a PCR amplification using the RBD-Vif-C as a template, ligating the obtained PCR product RBD-Vif-C to the expression vector pet-32a, and nucleic acid encoding the PTD being located on the N-terminus of the RBD-Vif-C to form a fusion expression vector PTD-RBD-Vif-C;

(5) transforming plasmids of the PTD-RBD-Vif-C into the *Escherichia coli* BL21(DE3);

(6) culturing the transformed *Escherichia coli*;

(7) a single PTD-RBD-Vif-C protein is obtained after a purification using a nickel column.

The construction of the vector mentioned in step (1) comprises steps as follows: synthesizing two pairs of primers according to nucleic acid encoding Vif protein of HIV-1 and KRAS protein respectively, then performing the PCR amplification with the aforementioned primers using a sequence of PNL4-3 plasmids of HIV-1 virus as the template; then cloning the PCR amplification product into the pcDNA3.1 by different enzyme cutting sites, wherein nucleic acid encoding segment of RBD is inserted into nucleic acid encoding the N-terminus of the Vif.

Culturing mentioned in step (6) is to inoculate a single colony of the transformed *Escherichia coli* to a LB liquid medium containing ampicillin for cultuting overnight; and then the colony is inoculated to the 37° C. preheated LB liquid medium containing ampicillin with a volume ratio of 1:50 for culturing until OD600 reaches 0.6; IPTG is added until having a final concentration of 0.4 mmol/L, the PTD-RBD-Vif-C protein expresses, and the bacteria is collected after induction.

A method of purification mentioned in step (7) is to wash total bacteria with PBS Buffer. After being resuspended and ultrasonic treated, a lysate supernatant is obtained by a high speed centrifugation, and an eluted protein is collected after an affinity chromatography purification using the nickel column.

Embodiment 2 the Protein Encoded by the Chimeric Vector RBD-Vif-C can Degrade the KRAS Protein and Inhibit its Signaling Pathway of Phosphorylation in the Downstream The mutant KRAS genes, KRAS-G12D and KRAS-G12V, are fusion expressed with the RFP gene respectively and are cloned into the vector of pcDNA3.1. The expression of the KRAS can be reflected by observing the expression of the RFP. Meanwhile, the expression of the KRAS is further verified by Western Blot.

(1) Co-transfecting the vector including nucleic acid encoding the KRAS-G12D-RFP with the vector RBD-Vif-C or the KRAS-G12V-RFP with the vector RBD-Vif-C in 293t cells in six-well plates, with a weight of plasmids of 1 μg; 48 hours after co-transfection, observing the expression of the RFP; meanwhile collecting a cell lysate for detecting the expression of the KRAS by the Western Blot.

The experiment shows that the RBD-Vif-C can degrade the mutant KRAS protein.

(2) Co-transfecting the vector including nucleic acid encoding the KRAS-G12D and the plasmid of the RBD-Vif-C in 293t cells in six-well plates; 48 hours later, collecting the cell lysate for detecting the expressions of ERK and phosphorylated ERK by the Western Blot.

The experiment shows that the RBD-Vif-C can inhibit its signaling pathway of phosphorylation in the downstream of the KRAS protein by degrading it.

Embodiment 3 Protein PTD-RBD-Vif-C has a Good Killing Effect on the Tumor Cells In Vitro In consideration of factors such as low efficiency of the transfection in cell plasmid system of pancreatic cancer, lung cancer and colorectal cancer, and subsequent druggability factor of protein, hence, *Escherichia coli* is chosen to express the corresponding RBD-Vif-C protein while GFP-Vif-C is chosen as a negative control protein, in order to attempt to verify the inhibition of the expression of KRAS gene by the RBD-Vif-C by means of the action mode of protein directly.

Firstly with reference to the methods from the related literatures, an effective transmembrane oligopeptide PTD is synthesized and the sequence thereof is shown in the drawings. Then nucleic acid encoding the transmembrane peptide and the vector RBD-Vif-C are cloned into a prokaryotic expression vector of pET-32a together, expressing the RBD-Vif-C protein by a prokaryotic system. The PTD-RBD-Vif-C protein with His-tag is purified by a nickel column and the protein with relatively high purity can be obtained after several optimizations, as shown in FIGS. 3-13. Further, endotoxin in the protein is removed by the method of Triton X-114. Since the protein itself has the transmembrane peptide, the purified protein can be directly added into the cell culture supernatant, which provides the subsequent experiments with greater convenience.

(1) Planking multiple cells into 24-well plates, after the cells being adhered; adding 4 μg/well of the PTD-RBD-Vif-C protein or the PTD-GFP-Vif-C protein respectively; after treating the cells for 48 hours, observing and recording growth states of the various cells with a microscope.

The experiment shows that PTD-RBD-Vif-C protein can inhibit the proliferation of various tumor cells related to the KRAS.

(2) Adding 0 μg/well, 2 μg/well, 4 μg/well and 8 μg/well of the PTD-RBD-Vif-C protein to the Panc-1 cells and the A549 cells in the 24-well plates respectively; collecting the cells after treating them for 48 hours; labeling flow antibody of Annexin-V FITC and detecting the apoptosis of these two kinds of cells.

The experiment shows the PTD-RBD-Vif-C protein can induce the apoptosis of tumor cells related to the KRAS and has a certain concentration gradient dependency.

(3) Adding 2 μg/well of the PTD-GFP-Vif-C protein and 2 μg/well of the PTD-RBD-Vif-C protein to the Panc-1 cells and the A549 cells in six-well plates respectively; after treating them for 12 hours, collecting cell lysate for detecting the expression of endogenous KRAS of these two kinds of cells by Western Blot.

The experiment shows that the PTD-RBD-Vif-C protein can inhibit the expression of the endogenous KRAS gene.

Embodiment 4 PTD-RBD-Vif-C Protein has a Good Anti-Tumor Effect in Mice

Six male Balb/c nude mice of 4-6 months old were ordered from the Animal Experimental Center of Sun Yat-sen University. They were divided into two groups randomly and each group contained three mice. The mice were subcutaneously inoculated with $1\times10^6$ of Panc-1 cells and A549 cells respectively to generate tumors. Two weeks later, subcutaneous generation of tumor in mice was observed, and the PTD-RBD-Vif-C protein and the PTD-GFP-Vif-C protein were started to be injected into the mice 2-3 times a week. Four weeks later, the mice were executed and tumor tissues were taken for observation and were recorded the weight.

The experiment shows that the PTD-RBD-Vif-C protein has a good anti-tumor effect in mice, especially in the tumor cells of pancreatic cancer and lung cancer.

Embodiment 5 the Acute Toxicity Test of the PTD-RBD-Vif-C Protein in Mice (1) 18 male Balb/c mice of 4-6 months old were ordered from the Animal Experimental Center of Sun Yat-sen University. They were divided into 3 groups randomly and each group contained 6 mice.

(2) The PTD-RBD-Vif-C protein was injected into the mice by means of tail vein injection with an injection dose of 0 mg/kg (PBS), 10 mg/kg and 20 mg/kg respectively, each group contained 6 mice.

(3) Two weeks later, blood samples of the mice were taken for detection of liver function and renal function, and the experiment result is noimal.

(4) After execution, each tissue samples of heart, liver, spleen, lung and kidney were taken from the mice to perform HE staining, in order to observe whether there was a lesion in the organ or not.

The experiment shows that 20 mg/kg dose of protein is non-toxic and safe for the mouse, and such protein has a better druggability.

Embodiment 6 the Construction Model of the Chimeric Vector Rev-Vif-C

Nucleic acid encoding two oligomerization binding domains (amino acids at positions 9-26 and amino acids at positions 51-65) on the HIV-1 Rev gene were respectively cloned to the N-terminus of the Vif gene, replaced nucleic acid encoding the binding sites (amino acids at positions 1-79) of APOBEC3G, and then were ligated to the vector of pcDNA3.1 to form three different chimeric vectors, which are named as ROL1-Vif-C, ROL2-Vif-C and ROL12-Vif-C respectively. In particular, ROL1 represents nucleic acid encoding the oligomerization binding domain of the N-terminus of the Rev, i.e. the amino acids at positions 9-26; ROL2 represents nucleic acid encoding the oligomerization binding domain of the C-terminus of the Rev, i.e. the amino acids at positions 51-65; and ROL12 represents nucleic acid encoding the two oligomerization binding domains tandem the N-terminus and C-terminus of the Rev, i.e. the amino acids at positions 9-26 and amino acids at positions 51-65.

Specific steps are as follows:

(1) Respectively replacing nucleic acid encoding the amino acid sequence at positions 1-79 of the N-terminus of the Vif protein with nucleic acid encoding two oligomerization domains provided on the protein structure of the Rev, thus three new chimeric vectors ROL1-Vif-C (containing nucleic acid encoding the oligomerization domain of the N-terminus of the Rev, i.e. the amino acids at positions 9-26), ROL2-Vif-C (containing nucleic acid encoding the oligomerization domain of the C-terminus of the Rev, i.e. the amino acids at positions 51-65) and ROL12-Vif-C (containing nucleic acid encoding two oligomerization domains of the N-terminus and C-terminus of the Rev, i.e. the amino acids at positions 9-65) were constructed.

(2) Cloning these three chimeric vectors into the expression vector pcDNA3.1 and performing a transient expression by transfection.

In particular, the construction of the vectors mentioned in step (1) comprises steps as follows: synthesizing 4 pairs of primers according to nucleic acid encoding the Vif protein and the Rev protein of HIV-1 respectively, then performing PCR amplification with the aforementioned primers using the sequence of the PNL4-3 plasmids of HIV-1 virus as template; then cloning the PCR amplification product into the pcDNA3.1 by different enzyme cutting sites, wherein nucleic acid encoding segment of the Rev is inserted into nucleic acid encoding the N-terminus of the Vif segment.

Embodiment 7 the Protein Encoded by the Chimeric Vector Rev-Vif-C Degrades Rev Protein by the Ubiquitination Pathway HIV-1 Rev gene was performed a fusion expression with the RFP gene and they were cloned into the vector of pcDNA3.1, thus the expression of the Rev can be reflected by observing the expression of the RFP; meanwhile the Rev gene was performed the fusion expression with a HA label in order to further verify the expression of Rev by the Western Blot.

(1) Co-transfecting the vector including nucleic acid encoding the Rev-RFP and the vector ROL1-Vif-C (or the ROL2-Vif-C or the ROL12-Vif-C) in the 293t cells in the 24-well plates with an amount of plasmids of 1:0, 1:1, 1:2 and 1:3 respectively; 48 hours after transfection, observing the expression of the RFP; meanwhile, co-transfecting the vector including nucleic acid encoding the Rev-HA and the vector ROL1-Vif-C in the 293t cells on the six-well plates with the amount of plasmids of 1:0, 1:1, 1:2 and 1:3 respectively; 48 hours after transfection, collecting the cell lysate for detecting the expression of Rev by the Western Blot.

The experiment shows that the proteins encoded by the three chimeric vectors can inhibit the expression of Rev protein and have a certain concentration gradient dependency.

(2) Co-transfecting 200 ng of the vector including nucleic acid encoding Rev-RFP and 200 ng of ROL12-Vif-C vector in the 293t cells in the 24-well plates; 24 hours later, adding 10 μM of MG132 to treat the cells; after treating them for 12 hours, observing the expression of the RFP.

(3) Co-transfecting 200 ng of the vector including nucleic acid encoding Rev-RFP and 200 ng of ROL12-Vif-C vector in the 293t cells in the 24-well plates; 6 hours later, transfecting 50 nM of si-NC, si-ElonginB, si-ElonginC and si-Culin5; 48 hours after transfection, observing the expression of the RFP.

(4) Co-transfecting 3 μg of Ub-Flag of the plasmid, 3 μg of the vector including nucleic acid encoding Rev-HA and 2 μg of ROL1-Vif-C, ROL2-Vif-C, ROL12-Vif-C vectors respectively in the 293t cells in the 6 cm plate; 48 hours after transfection, collecting the cell lysate for Co-IP to enrich the Rev-HA protein, and further detecting the ubiquitination of the Rev protein.

The above three experiments show that the protein encoded by the chimeric vectors degrade the Rev protein by the ubiquitination pathway mediated by the Vif.

Embodiment 8 the Protein Encoded by the Chimeric Vector Rev-Vif-C Inhibits the Replication of Various Viral Strains of Wild-Type HIV-1 by Inhibiting the Nuclear Export Function of the Rev-RRE There is a splicing donor SD and a splicing acceptor SA on PDM628. When the Rev protein is not present, the luciferase gene carried by the PDM628 is cleaved, causing a trace expression of luciferase. When two kinds of plasmids co-transfect, the Rev protein is combined with the RRE element and the luciferase gene segment is brought out of the cell nucleus in order to avoid being cleaved by SD and SA, and thus the luciferase expresses massively. Therefore, when the expression of Rev protein is inhibited, the system of nuclear export related to the Rev-RRE will be inhibited and the amount of expression of luciferase will decrease by this time. Based on such principle, it can be judged whether the function of the Rev protein is affected or not.

(1) Co-transfecting 10 ng of $_P$DM628 plasmids and 10 ng of Rev plasmids respectively in the 293t cells on 96-well plates, then co-transfecting different concentrations of ROL1-Vif-C, ROL2-Vif-C, ROL12-Vif-C and M10 plasmids; 48 hours after transfection, collecting the cell lysate to detect the expression of luciferase.

The experiment shows that proteins encoded by three chimeric vectors each can inhibit the system of nuclear export related to the Rev-RRE, and have a certain concentration gradient dependency. Meanwhile, the effect of the proteins encoded by the provided chimeric vectors is apparently better than the existing RevM10 mutant.

(2) Co-transfecting 50 ng of PNL4-3 plasmids and different concentrations of ROL1-Vif-C, ROL2-Vif-C, ROL12-Vif-C plasmids (50 ng, 100 ng, 150 ng) respectively in the 293t cells in 24-well plates; 48 hours after transfection, collecting the supernatant to detect the expression of P24 by ELISA. (B), Co-transfecting 50 ng of PYU-2 plasmids and different concentrations of ROL1-Vif-C, ROL2-

Vif-C, ROL12-Vif-C plasmids (50 ng, 100 ng, 150 ng) respectively in the 293t cells on the 24-well plate; 48 hours after transfection, collecting the supernatant to detect the expression of P24 by ELISA.

The experiment shows that proteins encoded by three chimeric vectors each can inhibit the replication of various different wild-types HIV-1, and have a certain concentration gradient dependency.

What is claimed is:

1. A fusion protein comprising a Rev or functional fragment thereof directly fused to a Vif protein lacking its N-terminal amino acids at positions 1-79 of SEQ ID NO:5.

2. The fusion protein of claim 1, wherein the N-terminal amino acids of Vif at positions 1-79 of SEQ ID NO: 5 are replaced with at least one oligomerization domain of the Rev protein.

3. The fusion protein of claim 2, wherein the at least one oligomerization domain of the Rev protein is the N-terminal oligomerization domain of the Rev protein.

4. The fusion protein of claim 3, wherein the N-terminal oligomerization domain of the Rev protein comprises amino acids 9-26 of SEQ ID NO: 6.

5. The fusion protein of claim 2, wherein the at least one oligomerization domain of the Rev protein is the C-terminal oligomerization domain of the Rev protein.

6. The fusion protein of claim 5, wherein the C-terminal oligomerization domain of the Rev protein comprises amino acids 51-65 of SEQ ID NO: 7.

7. The fusion protein of claim 2, wherein the at least one oligomerization domain of the Rev protein is both the N-terminal and the C-terminal oligomerization domains of the Rev protein.

8. The fusion protein of claim 7, wherein the N-terminal and C-terminal oligomerization domains of the Rev protein comprise amino acids 9-65 of SEQ ID NO: 8.

9. A composition comprising the fusion protein of claim 1 and a pharmaceutically acceptable carrier.

10. A nucleic acid molecule encoding the fusion protein of claim 1.

11. An expression vector comprising the nucleic acid molecule of claim 10.

12. A host cell comprising the expression vector of claim 11.

13. A method for making a fusion protein comprising a Rev or functional fragment thereof directly fused to a Vif protein lacking its N-terminal amino acids at positions 1-79 of SEQ ID NO:5, said method comprising:
culturing the host cell of claim 12 under conditions that result in the production of a fusion protein comprising a Rev or functional fragment thereof directly fused to a Vif protein or a functional fragment thereof; and
isolating the fusion protein from the host cell culture.

14. A fusion protein comprising a Raf or functional fragment thereof directly fused to a Vif protein lacking its N-terminal amino acids at positions 1-79 of SEQ ID NO:5.

15. The fusion protein of claim 14, wherein the N-terminal amino acids of Vif at positions 1-79 of SEQ ID NO: 5 are replaced with a binding domain of an N-terminus of the Raf protein which can specifically bind to GTP-Kras.

16. A composition comprising the fusion protein of claim 14 and a pharmaceutically acceptable carrier.

17. A nucleic acid molecule encoding the fusion protein of claim 14.

18. An expression vector comprising the nucleic acid molecule of claim 17.

19. A host cell comprising the expression vector of claim 18.

20. A method for making a fusion protein comprising a Raf or functional fragment thereof directly fused to a Vif protein lacking its N-terminal amino acids at positions 1-79 of SEQ ID NO:5, said method comprising:
culturing the host cell of claim 19 under conditions that result in the production of a fusion protein comprising a Raf or functional fragment thereof directly fused to a Vif protein or a functional fragment thereof; and
isolating the fusion protein from the host cell culture.

\* \* \* \* \*